United States Patent [19]

Scott

[11] Patent Number: 4,986,982

[45] Date of Patent: Jan. 22, 1991

[54] COSMETIC COMPOSITION

[76] Inventor: Ian R. Scott, 6 Holylake, Wellingborough, Northants NN8 3NZ, England

[21] Appl. No.: 351,747

[22] Filed: May 15, 1989

[30] Foreign Application Priority Data

May 13, 1988 [GB] United Kingdom ................ 8811408

[51] Int. Cl.$^5$ .............................................. A61K 7/48
[52] U.S. Cl. ...................................... 424/63; 514/423; 514/424; 514/785; 514/947
[58] Field of Search ...................... 424/61, 63, 64, 70, 424/59; 514/423, 424, 785, 788, 946, 947

[56] References Cited

U.S. PATENT DOCUMENTS

| | | | |
|---|---|---|---|
| 3,836,665 | 9/1974 | Eberhardt | 424/47 X |
| 4,774,255 | 9/1988 | Black et al. | 548/519 X |
| 4,832,946 | 5/1989 | Greer | 424/115 X |

FOREIGN PATENT DOCUMENTS

| | | |
|---|---|---|
| 176217 | 4/1986 | European Pat. Off. |
| 1567496 | 5/1980 | United Kingdom |

Primary Examiner—Merrell C. Cashion, Jr.
Assistant Examiner—Susan S. Rucker
Attorney, Agent, or Firm—Cushman, Darby & Cushman

[57] ABSTRACT

An aqueous composition for topical application to human skin comprises:
  (i) a special ester of pyroglutamic acid;
  (ii) a cosmetically acceptable aqueous buffer having an effective pH value of from 2 to <7; and
  (iii) optionally, other cosmetic adjuncts.

10 Claims, No Drawings

COSMETIC COMPOSITION

FIELD OF INVENTION

The invention relates to aqueous compositions containing an ester of pyroglutamic acid for topical application to human skin or hair.

BACKGROUND AND PRIOR ART

Pyroglutamic acid (also known as 2-pyrrolidone-5-carboxylic acid) is the principle ingredient of the "natural moisturising factor" that enables the stratum corneum of the skin to maintain a high water content despite low external humidity. Pyroglutamic acid applied topically to the skin has a temporary moisturising effect, but it is easily washed away and gives no long term skin benefit.

The use of certain esters of pyroglutamic acid as auxiliary agents for accelerating absorption of drugs through the skin is described in JA 60-214744 (Nitto Denki Kogyo KK.

Cosmetics containing one or more compounds obtained by the esterification of 2-pyrrolidone-5-carboxylic acid (PCA) and a fatty acid chosen from straight chain higher fatty acids are described in JA 57-185209 (Nisshin Seiyu KK) for contributing to the natural moisturising factor (NMF) present in the horny layer of the skin, part of which NMF is characterised as a salt of PCA.

Certain esters of pyroglutamic acid described in FP-A-0 176 217 (Unilever) are stated to be analogues of naturally occuring N-terminal pyroglutamic peptides. These naturally occurring peptides are substrates for the enzyme pyroglutamic acid peptidase which represent one route of pyroglutamic acid synthesis in the stratum corneum: [See: J G Barrett and I R Scott (1983), "Pyrrolidone carboxylic acid synthesis in guinea pig epidermis", J Invest. Dermatol. 81, 122].

These esters are stated to readily penetrate into the stratum corneum, and there provide a substrate for this enzyme at the normal site of pyroglutamic acid synthesis, that is, inside the cells of the stratum corneum.

There are, however, certain disadvantages in employing products based on these prior proposals; these are firstly, in aqueous systems, there is a tendency for hydrolysis of the ester of pyroglutamic acid to occur prematurely, so that the free acid, pyroglutamic acid, is present in the composition, and its benefit prior to application to the skin is thereby at best relatively short lived, and secondly, that the presence of drugs in topical products can severely limit their cosmetic usefulness.

We have now discovered that the stability of esters of pyroglutamic acid can be significantly improved and the general cosmetic use widened, by formulating them in an aqueous composition having an acid pH, preferably one which otherwise contains no molecule that could be classed as a drug, thereby limiting its cosmetic usefulness. Also, we have found that the ester of pyroglutamic acid penetrates more readily into the stratum corneum than does the free acid, the penetrated ester being enzymically cleaved, as already stated, to yield pyroglutamic acid in situ in the stratum corneum, thereby to auqment that which occurs naturally in this region of the skin. Evidence to support this observation is given later in this specification.

DEFINITION OF THE INVENTION

Accordingly, the invention provides an aqueous composition for topical application to human skin which comprises:

(i) from 0.01 to 99% by weight of an ester of pyroglutamic acid having the structure:

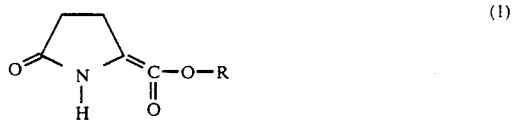
(1)

where R is a linear or branched chain saturated or unsaturated alkyl group having from 1 to 12 atoms, or the group:

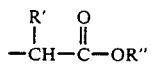

where R' and R" are the same or different and are each represented by H or the group:

(2)

where either u or v is 1 and the other of them is zero
w is zero, or an integer of from 1 to 21
x is zero, or an integer of from 1 to 4
y is zero, or an integer of from 1 to 2
z is zero, or an integer of from 1 to 4; and
u+v+w+x+y+z is an integer of from 1 to 22;
the subgroups within the group (2) being in any sequence; provided that when the subgroup (CH=CH) is present, then the total number of carbon atoms in said group (2) will be from 10 to 20; and (ii) from 1 to 99.99% by weight of a cosmetically acceptable aqueous buffer having an effective pH of from 2 to <7; and (iii) from 0 to 98.99% by weight of cosmetic adjuncts.

DISCLOSURE OF THE INVENTION

It is accordingly an object of the invention to provide a aqueous composition which is suitable for topical application to human skin, including the lips, mucosae scalp, and to human hair, comprising certain esters of pyroglutamic acid in an acidic buffer, to provide a source of pyroglutamic acid to the skin, in particular to the stratum corneum, following topical application.

THE ESTERS OF PYROGLUTAMIC ACID

Examples of suitable esters of pyroglutamic acid where R in structure (1) is a $C_1$ to $C_{12}$ linear or branched chain alkyl group are:
pyroglutamic acid methyl ester
pyroglutamic acid ethyl ester
pyroglutamic acid n-propyl ester
pyroglutamic acid n-butyl ester
pyroglutamic acid n-hexyl ester
pyroglutamic acid n-heptyl ester
pyroglutamic acid n-octyl ester
pyroglutamic acid n-nonyl ester
pyroglutamic acid n-decyl ester
pyroglutamic acid n-undecyl ester
pyroglutamic acid n-dodecyl ester
pyroglutamic acid iso-propyl ester pyroglutamic acid 2-methylhexyl ester
pyroglutamic acid 2-ethylhexyl ester
pyroglutamic acid 3,7-dimethyloctyl ester
pyroglutamic acid 2,4,4-trimethyl-1-pentane ester
pyroglutamic acid methyloctyl ester.

Particularly preferred esters of this group are those where R in structure (1) is $C_1$ to $C_6$ alkyl (linear or branched). Examples of the group (2) include straight and branched chain, saturated or unsaturated aliphatic groups having from 1 to 22 carbon atoms, such as the alkyl groups:
methyl
ethyl
propyl
iso-propyl
butyl
iso-butyl
n-valeryl
iso-valeryl
n-caproyl
n-heptyl
n-caprylyl
n-capryl
lauryl
myristyl
palmityl
stearyl
arachidyl, and
beheryl;
and the $C_{10-22}$ alkenyl groups:
linoleyl
linolenyl
γ-linolenyl
arachidonyl, and
columbinyl.

Examples of the group (2) also include hydroxyalkyl groups having from 1 to 22 carbon atoms, such as:
hydroxymethyl
2-hydroxyethyl
2-hydroxy-n-propyl
3-hydroxy-n-propyl
2-hydroxy-n-butyl
3-hydroxy-n-butyl
4-hydroxy-n-butyl
5-hydroxy-n-valeryl
6-hydroxy-n-caproyl
2,3-dihydroxy-n-propyl
2,3-dihydroxy-n-butyl
12-hydroxystearyl.

Further specific examples of esters of pyroglutamic acid containing the group:

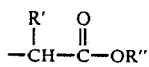

are:
2-[pyroglutamoyloxy]-propionic acid
methyl-2-[pyroglutamoyloxy]-acetate
ethyl-2-[pyroglutamoyloxy]-n-propionate
ethyl-2-[pyroglutamoyloxy1-n-butyrate
ethyl-2-[pyroglutamoyloxy]-iso-butyrate
ethyl-2-[pyroglutamoyloxy]-n-valerate
ethyl-2-[pyroglutamoyloxy]-n-caproate
ethyl-2-[pyroglutamoyloxy]-n-heptylate
ethyl-2-[pyroglutamoyloxy]-n-caprylate
ethyl-2-[pyroglutamoyloxy]-n-pelargonate
ethyl-2-[pyroglutamoyloxy]-3-hydroxybutyrate
iso-propyl-2-[pyroglutamoyloxy]-n-propionate
iso-propyl-2-[pyroglutamoyloxy]-n-caprylate
n-propyl-2-[pyroglutamoyloxy]-n-propionate
n-propyl-2-[pyroglutamoyloxy]-n-caprylate
stearyl-2-[pyroglutamoyloxy]-n-propionate
b 12-hydroxystearyl-2-[pyroglutamoylox]-n-propionate
stearyl-2-[pyroglutamoyloxy]-n-stearate
palmityl-2-[pyroglutamoyloxy]-n-propionate
linoleyl-2-[pyroglutamoyloxy]-n-propionate
linoleyl-2-[pyroglutamoyloxy]-n-caprylate
lauryl-2-[pyroglutamoyloxy]-n-caprylate
stearyl-2-[pyroglutamoyloxy]-n-caprylate
glyceryl mono(2-[pyroglutamoyloxy]-n-propionate)
glyceryl mono(2-[pyroglutamoyloxy]-n-caprylate), and
glyceryl di(2-[pyroglutamoyloxy]-n-propionate).

It is to be understood that the above list of specific examples of esters of pyroglutamic acid are not exhaustive, there being many other examples expressed by the generic structure of these esters.

The amount of the esters of pyroglutamic acid or mixtures thereof to be employed in accordance with the invention, will normally be from 0.01 to 99%, preferably from 0.1 to 20% and most preferably from 0.2 to 2% by weight of the composition.

THE AQUEOUS BUFFER

The composition also comprises a cosmetically acceptable aqueous buffer having an effective pH of from 2 to <7. Accordingly, the composition of the invention will acquire an acid pH determine by this buffer.

As has been stated earlier the stability of the ester of pyroglutamic acid during storage prior to use is enhanced in compositions having an acid pH, as compared with those having a neutral or alkaline pH, where some hyrolysis and premature release of free pyroglutamic acid can occur. Evidence in support of establishing a pH value of <7 is given later in this specification. Examples of suitable aqueous buffers include:
Citric acid - sodium citrate buffer having a pH of 4.0
Lactic acid - sodium lactate buffer having a pH of 4.0
Acetic acid - sodium acetate buffer having a pH of 4.0
Further details of the formulations of these buffers are given in the Examples.

It is to be understood that the forgoing buffers are only examples of suitable buffers and as such this does not represent an exhaustive list. Other buffers are available and suitable for using in accordance with the invention.

OTHER VEHICLES

The composition according to the invention can also optionally comprises a solid, semi-solid or liquid cosmetically and/or physiologically acceptable vehicle, in addition to the buffer, to enable the ester to be conveyed to the skin or hair at an appropriate dilution. The nature of the vehicle will depend upon the method chosen for topical administration of the composition. The vehicle can itself be inert or it can possess physiological or pharmaceutical benefits of its own.

The selection of a vehicle for this purpose presents a wide range of possibilities depending on the required product form of the composition. Suitable vehicles can be classified as described hereinafter.

It should be explained that vehicles are substances which can act as diluents, dispersants, or solvents for the esters which therefore ensure that they can be applied to and distributed evenly over the skin or hair at an appropriate concentration. The vehicle is preferably one which can aid penetration of the ester into the skin to reach the stratum corneum.

Vehicles that can be used in compositions according to the invention can include water and other liquids such as emollients and solvents, and also humectants and thickeners. Examples of each of these types of vehicles, which can be used singly or as mixtures of one or more vehicles, are as follows:

Emollients, such as stearyl alcohol, glyceryl monoricinoleate, glyceryl monostearate, propane-1,2-diol, butane-1,3-diol, mink oil, cetyl alcohol, ispropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, isopropyl myristate, isopropyl palmitate, isopropyl stearate, butyl stearate, polythylene glycol, triethylene glycol, lanolin, sesame oil, coconut oil, arachis oil, sunflower seed oil, evening primrose oil, castor oil, lanolin alcohols, petrolatum, mineral oil, butyl myristate, isostearic acid, palmitic acid, isopropyl linoleate, lauryl lactate, myristyl lactate, decyl oleate, myristyl myristate;

Propellants, such as trichlorofluoromethane, dichlorodifluoromethane, dichlorotetrafluoroethane, monochlorodifluoromethane, trichlorotrifluoroethane, propane, butane, isobutane, dimethyl ether, carbon dioxide, nitrous oxide;

Solvents, such as ethyl alcohol, methylene chloride, isopropanol, castor oil, ethylene glycol monoethyl ether, diethylene glycol monobutyl ether, diethylene glycol monoethyl ether, dimethyl sulphoxide, dimethyl formamide, tetrahydrofuran;

Humectants, such as glycerin, sorbitol, sodium 2-pyrrolidone-5-carboxylate, soluble collagen, dibutyl phthalate, gelatin;

Gelling agents such as soaps and fatty alcohols;

The amount of other (optional) vehicle in the composition, can comprise the balance of the composition, particularly where little or no other ingredients are present in the composition. Accordingly, the vehicle or vehicles can comprise up to 99.99%, preferably from 50 to 99.5% and ideally from 90 to 99% by weight of the composition.

PERFUME

The composition according to the invention can also optionally comprise a perfume in an amount sufficient to make the composition acceptable to the consumer and pleasant to use. Usually, the perfume when present will form from 0.01 to 10% by weight of the composition.

ACTIVITY ENHANCER

The composition according to the invention can also optionally comprise an activity enhancer, which can also function as a vehicle, and which can be chosen from a wide variety of molecules that can function in different ways to enhance delivery to the stratum corneum, of the ester or to potentiate its activity. Particular classes of activity enhancers include penetration enhancers and cationic polymers.

PENETRATION ENHANCERS

As has been stated earlier, the presence of a penetration enhancer can potentiate the benefit of the ester of pyroglutamic acid, by improving its delivery to the stratum corneum.

The penetration enhancer can accordingly function in a variety of ways. It can for example, improve the distribution of the ester on the skin surface or, it can increase its partition into the skin from the composition when applied topically, so aiding its passage to its site of action. Other mechanisms enhancing the benefit of the chemical inhibitor may also be involved.

Examples of penetration enhancers include:
2-methyl propan-2-ol
Propan-2-ol
Ethyl-2-hydroxypropanoate
Hexan-2,5-diol
POE(2) ethyl ether
Di(2-hydroxypropyl) ether
Pentan-2,4-diol
Acetone
POE(2) methyl ether
2-hydroxypropionic acid
2-hydroxyoctanoic acid
Propan-1-ol
1,4 Dioxane
Tetrahydrofuran
Butan-1,4-diol
Propylene glycol dipelargonate
Polyoxypropylene 15 stearyl ether
Octyl alcohol
POE ester of oleyl alcohol
Oleyl alcohol
Lauryl alcohol
Dioctyl adipate
Dicapryl adipate
Diisopropyl adipate
Diisopropyl sebacate
Dibutyl sebacate
Diethyl sebacate
Dimethyl sebacate
Dioctyl sebacate
Dibuyl suberate
Dioctyl azelate
Debenzyl sebacate
Dibutyl phthalate
Dibutyl azelate
Ethyl myristate
Dimethyl azelate
Butyl myristate
Dibutyl succinate
Didecyl phthalate
Decyl oleate
Ethyl caproate
Ethyl salicylate
Isopropyl palmitate
Ethyl laurate
2-ethyl-hexyl pelargonate
Isopropyl isostearate
Butyl laurate
Benzyl benzoate
Butyl benzoate
Hexyl laurate
Ethyl caprate
Ethyl caprylate
Butyl stearate
Benzyl salicylate
2-hyroxyoctanoic acid,
Further examples of penetration enhancers include:
Dimethyl sulphoxide
N,N-Dimethyl acetamide N,N-Dimethyl formamide
2-Pyrrolidone
1-Methyl-2-pyrrolidone
5-Methyl-2-pyrrolidone
1,5-Dimethyl-2-pyrrolidone
1-Ethyl-2-pyrrolidone
Phosphine oxides
Sugar esters
Tetrahydrofurfural alcohol
Urea
Diethyl-m-toluamide, and
1-Dodecylazacyloheptan-2-one Further examples of penetration enhancers include surface active agents, preferred examples of which include:

(i) Anionic surface active agents, such as metallic or alkanolamine salts of fatty acids for example sodium laurate and triethanolamine oleate;
alkyl benzene sulphonates, for example triethanolamine dodecyl benzene sulphonate;
alkyl sulphates, for example sodium lauryl sulphate;
alkyl ether sulphates, for example sodium lauryl ether sulphate [2 to 8 EO];
sulphosuccinates, for example sodium dioctyl sulphonsuccinate;
monoglyceride sulphates, for example sodium glyceryl monostearate monosulphate;
isethionates, for example sodium isethionate;
methyl taurides, for example Igepon T;
acylsarcosinates, for example sodium myristyl sarcosinate;
acyl peptides, for example Maypons and Lamepons; acyl lactylates,
polyalkoxylated ether glycollates, for example trideceth-7 carboxylic acid;
phosphates, for example sodium dilauryl phosphate.

(ii) Cationic surface active agents, such as amine salts, for example sapamin hydrochloride;
quartenary ammonium salts, for example Quaternium 5, Quaternium 31 and Quaternium 18;

(iii) Amphoteric suface active agents, such as imidazol compounds, for example Miranol;
N-alkyl amino acids, such as sodium cocaminopropionate and asparagine derivatives;
betaines, for example cocoamidopropylbetaine (iv) Nonionic surface active agents, such as fatty acid alkanolamides, for example oleic ethanolamide;
esters of polyalcohols, for example Span;
polyglycerol esters, for example that esterified with $C_{12-18}$ fatty acids and one or several OH groups;
polyalkoxylated derivatives, for example polyoxy-:polyoxyethylene stearate, and octylphenoxy polyethoxyethanol (TRITON X-100); ethers, for example polyoxyethylene lauryl ether;
ester ethers, for example Tween;
amine oxides, for example coconut and dodecyl dimethyl amine oxides.

Mixtures of two or more of the above surface active agents can be employed in the composition according to the invention.

(c) cationic polymers chosen from:
Guar Hydroxypropyltrimonium chloride
Quaternium-19
Quaternium-23
Quaternium-40
Quaternium-57
Poly(dipropyldiallylammonium chloride)
Poly(methyl-$\beta$-propaniodiallylammonium chloride)
Poly(diallylpiperidinium chloride)
Poly(vinyl pyridinium chloride)
Quaternised poly (vinyl alcohol)
Quaternised poly (dimethylaminoethylmethacrylate); and mixtures thereof.

The amount of activity enhancer, when employed in accordance with the invention, will normally be from 0.1 to 50%, preferably from 0.5 to 25% and most preferably from 0.5 to 10% by weight of the composition.

FURTHER OPTIONAL INGREDIENTS

The composition according to the invention can also optionally contain further ingredients in addition to those which are conventionally used for the provision of the cosmetically - acceptable vehicle.

Accordingly, in addition to ingredients conventionally used in preparing a lotion, cream, ointment, gel, powder, solid stick and aerosol concentrate, the composition can optionally comprise further ingredients such as a colourant, preservative, antioxidant, emollient or aerosol propellnnt, in amounts which are conventional in the cosmetics or pharmaceutical art.

PREPARATION OF THE COMPOSITION

The composition of the invention can be prepared in the form of a solution, lotion, gel, cream, ointment, solid stick or aerosol, or in any other form suited to administration topically to human skin.

When the composition is a liquid, such as a lotion or aerosol, or a semi-liquid such as a gel, cream or ointment, or a solid stick, then it is usually necessary to dissolve an effective quantity of the ester of pyroglutamic acid, or a mixture thereof, in water or ethanol or other aqueous or non-aqueous cosmetically acceptable vehicle, and then to admix this solution, if desired, in a conventional manner with a suitable cream or ointment base containing, for example an oil or silicone oil and water, or stick base containing a gelling agent such as sodium stearate, or with a normally liquefiable gaseous propellant in order to prepare the composition.

If desired, other cosmetically acceptable carriers, diluents or emollients can be incorporated in the therapeutic composition according to the invention, in order to facilitate even distribution over the skin or hair at a suitable concentration.

EVIDENCE TO SUPPORT REQUIREMENT OF ACID PH VALUE FOR IMPROVED STABILITY OF THE ESTER OF PYROGLUTAMIC ACID

As has been stated earlier, the stability of the ester of pyroglutamic acid during storage prior to use is enhanced in compositions having an acid pH, compared with those having a neutral or alkaline pH. It is accordingly apparent that hydrolysis of the ester with premature release of free pyroglutamic acid can occur faster at higher pH values than at lower values. Compositions having maximum skin benefit are therefore those having a pH value of <7 containing the unchanged ester of pyroglutamic acid with minimal free pyroglutamic acid.

In order to demonstrate the effect of pH on the stability of esters of pyroglutamic acid, the half-life of selected esters at selected pH values was measured as follows:

(i) The chosen ester of pyroglutamic acid was dissolved in aqueous buffer of a selected pH value, to provide a 0.1% w/v solution of the ester;

(ii) Intact (unhydrolysed) ester was analysed by high performance liquid chromatography at regular time intervals.

(iii) The log of the amount of the ester remaining intact versus time was plotted to give a straight line response.

(iv) From this plot, the time required for half of the ester of pyroglutamic acid to be hydrolysed (half of the ester remaining intact), can be determined if necessary by extrapolation.

Using this method, the half-life of selected esters of pyroglutamic acid was determined and the results obtained were as follows:

TABLE 1

STABILITY OF VARIOUS ALKYL ESTERS OF PYROGLUTAMIC ACID*

| ESTER | HALF LIFE IN HOURS | |
|---|---|---|
| | pH 7.0 | pH 4.0 |
| Ethyl-2-[pyroglutamoyloxy]-n-propionate | 9 | 1,700 |
| Pyroglutamic acid ethyl ester | 58 | 11,000 |
| Pyroglutamic acid n-butyl ester | 80 | 15,000 |
| Pyroglutamic acid n-hexyl ester | 96 | 18,000 |
| Pyroglutamic acid n-octyl ester | 96 | 18,000 |

*Assay performed in 100 mM phosphate buffer at 30° C.

The half-life of pyroglutamic acid ethyl ester was also determined over a narrower range of pH values on either side of neutrality to illustrate the importance of selecting a pH value for improved stability of <7.

TABLE 2

STABILITY OF PYROGLUTAMIC ACID ETHYL ESTER AT pH VALUES NEAR NEUTALITY

| pH value | Half-life (days) |
|---|---|
| 6.5 | 12 |
| 6.8 | 7 |
| 7.0 | 2.4 |
| 7.4 | 2 |
| 7.8 | 1 |

The above results in Tables 1 and 2 indicate that there is a rapid fall-off in stability of esters of pyroglutamic acid with increasing pH value. Ideally, compositions according to the invention should be shelf stable for at least one year, which involves selection of a suitable pH value to enable the chosen esters of pyroglutamic acid to have a half-life of at least one year.

EVIDENCE TO SUPPORT BENEFIT OF TOPICAL APPLICATION TO SKIN OF THE ESTER OF PYROGLUTAMIC ACID VERSUS THE FREE ACID

When pyroglutamic acid is applied topically to human skin, only a negligible amount is able to penetrate to the stratum corneum to augment that naturally present in this region of the skin. However, certain esters of pyroglutamic acid are able readily to penetrate the skin to reach the stratum corneum, where naturally occuring esterases cleave the ester to yield the free pyroglutamic acid which can then augment that which is naturally present in the skin, with the consequence that skin benefit is improved.

Delivery of esters of pyroglutamic acid, with subsequent hydrolysis to yield free pyroglutamic acid in the stratum corneum, was confirmed using tritiated esters of pyroglutamic acid and a radio-tracer technique.

Accordingly, [$^3$H] esters of pyroglutamic acid were each dissolved at 1% w/v in anhydrous ethanol or in an oil-in-water emulsion base. These solutions were then applied to the arms of volunteers, left for 18 horrs, washed with soap and water, and the stratum corneum was removed by stripping with Sellotape. The [$^3$H] pyroglutamic acid was separated from unchanged ester by chromotography on AG1X8 resin and the amount delivered to the skin expressed as nmoles per mg of stratum corneum protein.

The result obtained are summarised in Table 3:

TABLE 3

| Ester of Pyroglutamic acid | Pyroglutamic acid delivered (n mol/mg protein) | |
|---|---|---|
| | Ethanol base | Cream base |
| Ethyl | 8 | 5 |
| Butyl | 6 | 2 |
| Hexyl | 5 | 2 |
| Octyl | 4 | 1 |
| Dodecyl | 4 | 1 |

When [$^3$H] pyroglutamic acid instead of a corresponding ester was applied topically in this experiment, a negligible amount of the tritiated free acid was recovered from the stratum corneum.

The above results (Table 3) indicate that pyroglutamic acid is effectively delivered to the stratum coprneum following topical application of an ester thereof, while little pyroglutamic acid reached the stratum corneum if applied as the free acid. These results also indicate a preference for short alkyl chain esters, since the shorter the alkyl chain of the ester, the more effective is the delivery of the ester to the stratum corneum, as judged by the higher yield of pyroglutamic acid found in that region of the skin.

EXAMPLES

The invention is further illustrated by the following examples.

EXAMPLE 1

| BUFFERED SKIN CARE FORMULATION NO 1. 1. Base Formulation for Buffer | |
|---|---|
| Ingredient | % by wt |
| triglycerides | 31.0 |
| glyceryl stearate | 6.0 |
| cetyl alcohol | 1.2 |
| stearic acid | 2.0 |
| lanolin | 4.0 |
| propylene glycol | 2.0 |
| preservative | 0.3 |
| fragrance | 0.4 |
| Pyroglutamic acid ethyl ester | 1.0 |
| BUFFER 'A' | qv |
| deionized water | balance to 100.00 |
| pH = 4.0 | |
| Buffer 'A' : Citric acid-sodium citrate | |
| citric acid | 1.38 |
| Na citrate | 1.01 |
| pH adjusted to 4.0 with 0.1M citric acid or 0.1M sodium citrate. | |

EXAMPLE 2

| BUFFERED SKIN CARE FORMULATION NO 2. 1. Base Formulation for Buffer | |
|---|---|
| Ingredient | % by wt |
| triglycerides | 31.0 |

-continued

BUFFERED SKIN CARE FORMULATION NO 2.
1. Base Formulation for Buffer

| Ingredient | % by wt |
|---|---|
| glyceryl stearate | 6.0 |
| cetyl alcohol | 1.2 |
| stearic acid | 2.0 |
| lanolin | 4.0 |
| propylene glycol | 2.0 |
| preservative | 0.3 |
| fragrance | 0.4 |
| Pyroglutamic acid hexyl ester | 3.0 |
| BUFFER 'B' | qv |
| deionized water | balance to 100.00 |
| pH = 4.0 | |
| Buffer 'B' : Lactic acid-sodium lactate | |
| lactic acid (1M) | 0.90 sodium |
| lactate (1M) | 0.75 |
| pH adjusted to 4.0 with 0.1M lactic acid or 0.1M sodium lactate. | |

EXAMPLE 3

BUFFERED SKIN CARE FORMULATION NO 3.
1. Base Formulation for Buffer

| Ingredient | % by wt |
|---|---|
| triglycerides | 31.0 |
| glyceryl stearate | 6.0 |
| cetyl alcohol | 1.2 |
| stearic acid | 2.0 |
| lanolin | 4.0 |
| propylene glycol | 2.0 |
| preservative | 0.3 |
| fragrance | 0.4 |
| ethyl -2 [pyroglutamoyloxy]-n-propionate | 3.0 |
| BUFFER 'C' | qv |
| deionized water | balance to 100.00 |
| pH = 4.0 | |
| Buffer 'C' : Acetic acid-sodium acetate | |
| acetic acid (1M) | 8.2 |
| Sodium acetate | 0.25 |
| pH adjusted to 4.0 with 0.1M acetic acid or 0.1M Sodium acetate. | |

What is claimed is:

1. An aqueous composition for topical application to human skin which comprises:
   (i) from 0.01 to 99% by weight of an ester of pyroglutamic acid having the structure:

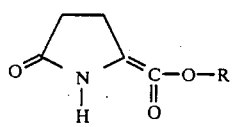 (1)

where R is a linear or branched chain saturated or unsaturated alkyl group having from 1 to 12 atoms,

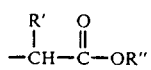

or the group:
where R' and R" are the same different and are each represented by H or the group:

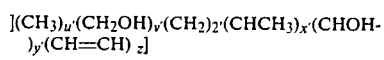 (2)

where ]u is zero, or 1 v is zero, or 1]
either u or v is 1 and the other of them is zero
w is zero, or an integer of from 1 to 21
x is zero, or an integer of from 1 to 4
y is zero, or an integer of from 1 to 2
z is zero, or an integer of from 1 to 4; and
u+v+w+x+y+z is an integer of from 1 to 22; the subgroups within the group (2) being in any sequence; provided that when the subgroup (CH=CH) is present, then the total number of carbon atoms in said group (2) will be from 10 to 20; and
   (ii) from 1 to 99.9% by weight of a cosmetically acceptable aqueous buffer having an effective pH of from 2 to <7; and
   (iii) from 0 to 98.99% by weight of cosmetic adjuncts.

2. The composition of claim 1, wherein the ester of pyroglutamic acid is chosen from those where R in Structure (1) is a $C_1$ to $C_{12}$ linear or branched chain alkyl group.

3. The composition of claim 2, wherein the ester of pyroglutamic acid is selected from the group consisting of:
pyroglutamic acid methyl ester
pyroglutamic acid ethyl ester
pyroglutamic acid n-propyl ester
pyroglutamic acid n-butyl ester
pyroglutamic acid n-hexyl ester
pyroglutamic acid n-heptyl ester
pyroglutamic acid n-octyl ester
pyroglutamic acid n-nonyl ester
pyroglutamic acid n-decyl ester
pyroglutamic acid n-undecyl ester
pyroglutamic acid n-dodecyl ester
pyroglutamic acid iso-propyl ester
pyroglutamic acid 2-methylhexyl ester
pyroglutamic acid 2-ethylhexyl ester
pyroglutamic acid 3,7-dimethyloctyl ester
pyroglutamic acid 2,4,4-trimethyl-1-pentane ester
pyroglutamic acid methyloctyl ester, and
mixtures thereof.

4. The composition of claim 1, wherein the R group in structure (1) is represented by group (2).

5. The composition of claim 4, wherein the group (2) is chosen from straight or branched chain, saturated or unsaturated aliphatic groups having from 1 to 22 carbon atoms, or from alkenyl groups having from 10 to 22 carbon atoms.

6. The composition of claim, 1, in which the ester of pyroglutamic acid is selected from the group consisting of:
2-[pyroglutamoyloxy]-propionic acid
methyl-2-[pyroglutamoyloxy]-acetate
ethyl-2-[pyroglutamoyloxy]-n-propionate
ethyl-2-[pyroglutamoyloxy]-n-butyrate
ethyl-2-[pyroglutamoyloxy]-iso-butyrate
ethyl-2-[pyroglutamoyloxy]-n-valerate
ethyl-2-[pyroglutamoyloxy]-n-caproate
ethyl-2-[pyroglutamoyloxy]-n-heptylate
ethyl-2-[pyroglutamoyloxy]-n-caprylate
ethyl-2-[pyroglutamoyloxy]-n-pelargonate
ethyl-2-[pyroglutamoyloxy]-3-hydroxybutyrate
iso-propyl-2-[pyroglutamoyloxy]-n-propionate
iso-propyl-2-[pyroglutamoyloxy]-n-caprylate
n-propyl-2-[pyroglutamoyloxy]-n-propionate
n-propyl-2-[pyroglutamoyloxy]-n-caprylate
stearyl-2-[pyroglutamoyloxy]-n-propionate 12-hydroxystearyl-2-[pyroglutamoyloxy]-n-propionate
stearyl-2-[pyroglutamoyloxy]-n-stearate
palmityl-2-[pyroglutamoyloxy]-n-propionate
linoleyl-2-[pyroglutamoyloxy]-n-propionate
linoleyl-2-[pyroglutamoyloxy]-n-caprylate
lauryl-2-[pyroglutamoyloxy]-n-caprylate
stearyl-2-[pyroglutamoyloxy]-n-caprylate
glyceryl mono(2-[pyroglutamoyloxy]-n-propionate)
glyceryl mono(2-[pyroglutamoyloxy]-n-caprylate)
glyceryl di(2-[pyroglutamoyloxy]-n-propionate), and mixtures thereof.

7. The composition of claim 1, wherein the amount of the ester of pyroglutamic acid is from 0.01 to 20% by weight of the composition.

8. The composition of claim 1, wherein the buffer is chosen from:
a citric acid - sodium citrate buffer having a pH of 4.0
a lactic acid - sodium lactate buffer having a pH of 4.0, and
an acetic acid - sodium acetate buffer having a pH of 4.0

9. The composition of claim 1, which additionally comprises from 0.01 to 10% by weight of a perfume.

10. The composition of claim 1, which further comprises 0.1 to 50%, by weight of the composition, of an activity enhancer chosen from penetration enhancers, surface active agents and cationic polymers.

* * * * *